US00PP30902P2

(12) United States Plant Patent
Hansen

(10) Patent No.: US PP30,902 P2
(45) Date of Patent: Sep. 24, 2019

(54) ***HOSTA* PLANT NAMED 'AGE OF GOLD'**

(50) Latin Name: ***Hosta* hybrid (Tratt.)**
Varietal Denomination: Age of Gold

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/998,376

(22) Filed: Aug. 10, 2018

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
CPC ..... A01H 5/02; A01H 5/12; A01H 5/0272; A01H 6/12; A01H 6/56
See application file for complete search history.

*Primary Examiner* — June Hwu

(57) ABSTRACT

A new and distinct *Hosta* plant named 'Age of Gold' with large, round-mounded habit with foliage of heavy substance, chartreuse to golden color, cordate-shaped with acute to apiculate apices. Flowers are soft pale lavender to near white with buds of light to medium lavender and persistent foliar bracts nearly matching coloration of flower buds and then becoming chartreuse as seeds mature. Scapes are outwardly holding flowers just above foliage.

1 Drawing Sheet

Latin name and variety denomination of the plant:
Botanical classification: *Hosta* hybrid (Tratt.).
Variety denomination: 'Age of Gold'.

BACKGROUND AND ORIGIN OF THE PLANT

The present invention relates to a new and distinct *hosta* plant, *Hosta* 'Age of Gold' hereinafter also referred to as the new plant or just the cultivar name, 'Age of Gold'. *Hosta* 'Age of Gold' was hybridized by the inventor as a cross between the unreleased proprietary hybrid WGI-40-B (not patented) as the female and *Hosta* 'American Sweetheart' (not patented) at a wholesale nursery greenhouse in Zeeland, Mich., USA on Jun. 30, 2010 and seeds were harvested on September of 2010 and sown in February of 2011. The new plant was given the breeder code H10-349-1 in the evaluation process. The new plant has been asexually propagated by division at the same nursery in Zeeland, Mich., USA since 2015 and also by careful shoot tip tissue culture with the resultant asexually propagated plants having retained all the same traits as the original plant. *Hosta* 'Age of Gold' is stable and reproduces true to type in successive generations of asexual reproduction.

No plants of *Hosta* 'Age of Gold' have been sold, under this or any other name, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

There are over 5,800 registered *hosta* cultivars with The American *Hosta* Society, which is the International Cultivar Registration Authority for the genus *Hosta* along with a similar number of unregistered cultivars. The nearest comparison varieties are *Hosta* 'Abiqua Recluse' (not patented), 'Coast to Coast' U.S. Plant Pat. No. 26,469, 'Fort Knox' (not patented), 'Golden Sculpture' (not patented), 'Piedmont Gold' (not patented) and 'Key West' (not patented). 'Abiqua Recluse' has lighter golden foliage with more dimpling between the veins and the flower scapes are more upright with smaller floral bracts that are more green. 'Coast to Coast' is a larger plant with lighter golden foliage having more dimpling between the veins, the flowers and flower bracts are more medium lavender and the scapes are more upright. 'Fort Knox' has foliage that develops to a lighter golden color, the scapes are more upright, and floral bracts are more chartreuse and not persistent. 'Golden Sculpture' has broader, brighter golden foliage with more dimpling between the veins. 'Piedmont Gold' has brighter golden foliage with slightly wavy margins, more dimpling, and more downward arching of the leaf blades. 'Key West' is larger in habit and the foliage is both larger and longer.

Comparison with the female parent has very large green leaves with streaked variegation. The male parent, 'American Sweetheart' is variegated with foliage having broad deep green margins and creamy white centers while the flowers are larger, more open and medium lavender on very upright scapes.

Other *Hosta* cultivars have chartreuse to golden foliage, but 'Age of Gold' is distinct from the above mentioned *hostas* and all other cultivars known to the discoverer by the following combined traits:

1. Large round-mounded plant with foliage of chartreuse to golden coloration;
2. Foliage with heavy substance;
3. Soft pale lavender to near white flowers just above foliage effective for about five weeks beginning in late June;
4. Outwardly extending scapes producing flowers just above foliage;

5. Scapes with large, persistent, floral bracts beginning light lavender as flowers open and developing to chartreuse with seed maturing.

BRIEF DESCRIPTION OF THE DRAWINGS

The photographs of *Hosta* 'Age of Gold' demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
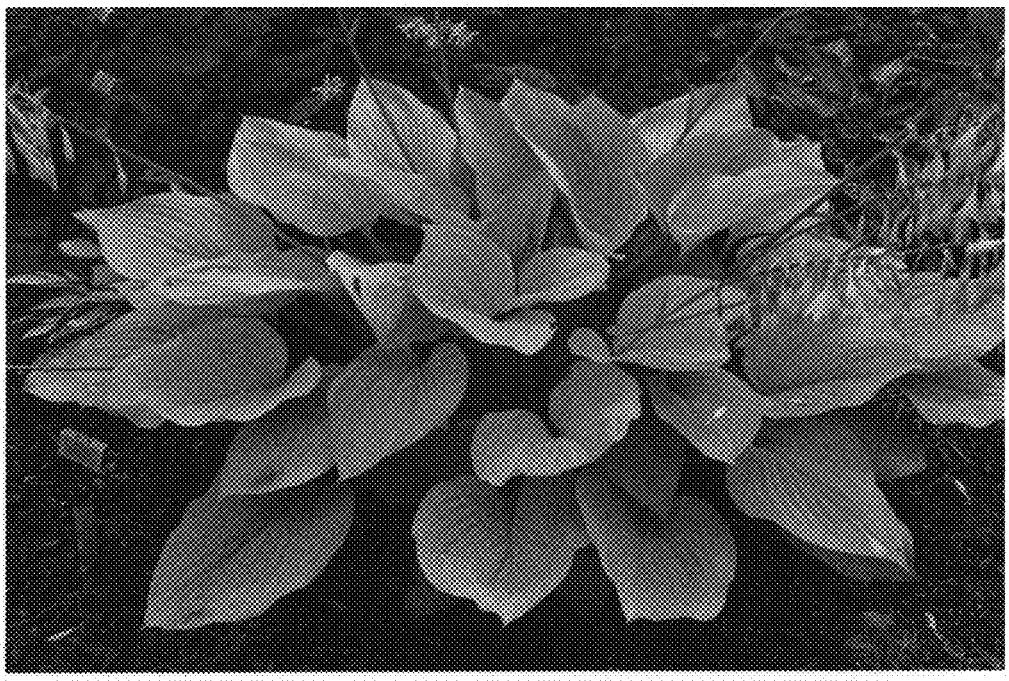
FIG. 1 shows a seven-year-old plant grown in a shaded trial garden in flower.
Figure 2:
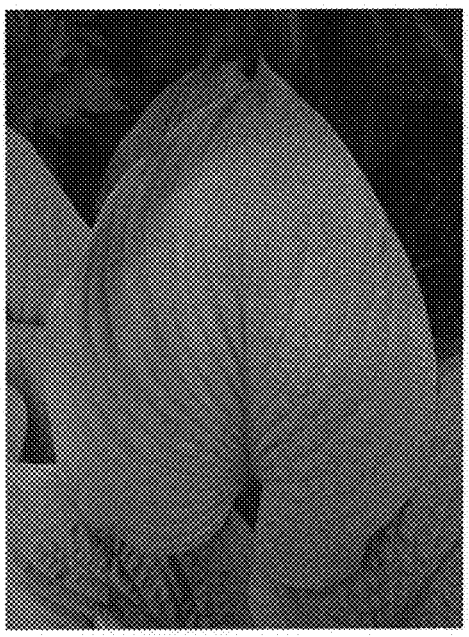
FIG. 2 shows a close-up of a leaf.
Figure 3:
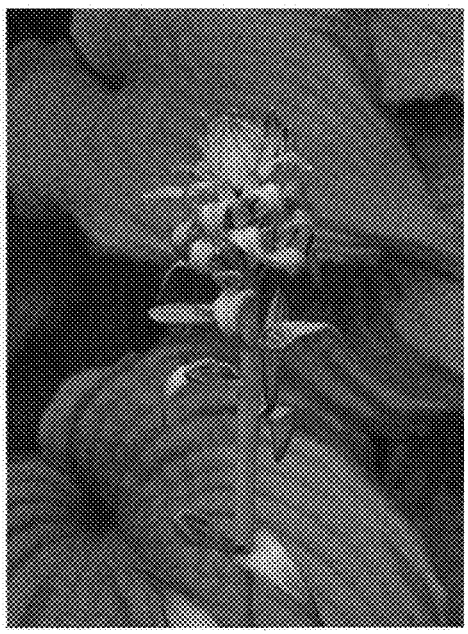
FIG. 3 shows a close-up of the flower scape showing buds and matching foliar bracts.

The following descriptions and color references are based on the 2015 edition of The Royal Horticultural Society Colour Chart except where common dictionary terms are used. The new plant, *Hosta* 'Age of Gold', has not been observed under all possible environments. The phenotype may vary slightly with different environmental conditions, such as temperature, light, fertility, moisture and maturity levels, but without any change in the genotype. The following observations and size descriptions are of a potted three-year old plant in a shaded greenhouse in Zeeland, Mich. with supplemental water and fertilizer.

Botanical classification: *Hosta* hybrid;

Parentage: Female or seed parent is the proprietary, unreleased hybrid WGI-40-B, which is a hybrid involving *Hosta nigrescens* 'Elatior' (not patented); male or pollen parent is 'American Sweetheart';

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching;

Plant shape and habit: Hardy herbaceous perennial with basal rosette of leaves emerging from rhizomes producing a large symmetrical rounded-mound of leaves;

Plant size: Foliage height about 78.0 cm above soil line to the top of the leaves and about 160.0 cm wide at the widest point slightly above the soil line; about 95.0 cm to top flowers;

Foliage description: Cordate; acute to acuminate apex with cordate base; glabrous; glaucous abaxial and slightly lustrous adaxial when mature, as emerging abaxial is lustrous and adaxial matte; margin entire and flat; surface slightly dimpled above;

Leaf blade size: To about 36.0 cm long and 30.5 cm wide, average about 32.0 cm long and 28.5 cm wide;

Leaf blade color: Variable with season and light exposure; early season and shortly after emerging adaxial nearest blend between RHS N144D and RHS 146D; early season and shortly after emerging abaxial nearest RHS 146D; mid-season and later summer adaxial some regions with more light nearest RHS 153D, others in more shade or beneath another leaf nearest N144A; mid-season and later abaxial blend between RHS 146D and RHS N144A;

Petiole: Entire; glabrous; glaucous abaxial and matte adaxial; concavo-convex; outwardly from base of plant to leaf base, stiff; to about 62.5 cm long and at base 20.0 mm across and 18.0 mm deep; average 58.0 cm long and base 18.0 mm wide and 16.0 mm deep;

Petiole color: Adaxial and abaxial between RHS 145C and RHS 145B;

Veins: Parallel, camptodrome; lightly impressed adaxial, slightly ribbed abaxial; 14 to 15 pairs with one midrib, average 14 pairs;

Veins color: Emerging adaxial nearest RHS 148B and abaxial nearest RHS 146D; mature adaxial nearest RHS 146D and abaxial nearest RHS 146D;

Flower description:

Buds one day prior to opening: Clavate with rounded apex and narrow tubular base; about 55.0 mm long, apical bulb about 11.5 mm diameter and tube about 3.0 mm diameter;

Bud color: One day prior to opening nearest RHS 85D; seven days prior to opening nearest RHS N87D Inflorescence: Average flowering portion 36.0 cm long and 8.5 cm wide;

Flowers: Perfect; single; campanulate, funnelform; actinomorphic; attitude slightly drooping; about 2.8 cm wide and 6.0 cm long, fused tube portion about 2.2 cm long and 3.5 mm diameter (distal flowers smaller); persistent; effective for a normal period, usually one day on plant or as cut flower; scapes remain effective with flowers beginning early summer for about five weeks; about 62 flowers per scape; average spacing between flowers about 0.5 cm, significantly greater in proximal flowers;

Floral bracts: Lanceolate; acute apex; truncate sessile base; concavo-convex; persistent; viridescent with seed maturing; to about 5.5 cm long and 19.0 mm wide decreasing distally, average about 2.8 cm long and 10.0 mm across;

Floral bract color: Upon anthesis nearest RHS 76C abaxial and adaxial; developing to nearest RHS 146C abaxial and adaxial with seed maturing;

Flower fragrance: None detected;

Corolla size: About 55.0 mm long and 28.0 wide, decreasing distally;

Corolla tube size: About 22.0 mm long and 3.5 mm diameter, decreasing distally;

Tepal: Six; two nearly identical sets of three, glabrous, entire; acute apex with puberulent tuft; fused in basal 33.0 mm; inner set with translucent margin about 1.5 mm wide; approximately 4.5 cm long and about 1.2 cm wide;

Tepal color: Coloring of both sets adaxial longitudinal center about 4.0 mm wide nearest RHS 85D and longitudinal edge nearest RHS NN155D without obvious veins; abaxial blend between RHS NN155D and RHS 85D; abaxial tube blend between RHS NN155D and RHS 85D;

Gynoecium: Single; tri-carpelled;

*Style*.—Single, approximately 6.4 cm long, 1.0 mm diameter, curved upward about 90° in distal 0.5 cm; color nearest RHS 155A.

*Stigma*.—Globose, about 1.5 mm in diameter; color nearest RHS NN155A.

*Ovary*.—Ellipsoidal; longitudinally fluted, about 7.0 mm long and 3.0 mm diameter at widest; rounded apex and truncate base; color nearest RHS 145A.

Androecium:

*Filaments*.—Six, approximately 5.0 cm long and 0.8 mm in diameter; curved upward in the apical 10.0 mm; color nearest RHS 145D proximally and nearest RHS 155D distally.

*Anthers*.—Elliptic; dorsifixed, longitudinally dehiscent; about 4.0 mm long and 1.0 mm wide; color nearest RHS 163C.

*Pollen*.—Abundant; elliptic, less than 0.1 mm long; color nearest RHS 21A.

Peduncle: Usually one per mature division; glaucous, glabrous to becoming slightly, lustrous later in season; outwardly; about 128.0 cm long, and up to about 15.0 mm in diameter at base; average about 120.0 cm tall and about 14.0 mm diameter at base;

Peduncle color: When flowering nearest RHS 146D below foliage and nearest RHS 146B distally;

Pedicel: Glabrous; terete; secund; up to 20.0 mm long and 2.0 mm diameter, average about 12.0 mm long and 1.5 mm diameter; attitude slightly drooping; color nearest blend of nearest RHS 76C and RHS 194D;

Fruit: Tri-valved dehiscent capsule; oblong elliptic, about 3.4 cm long and 7.0 mm diameter, with thin beak about 0.5 mm diameter extending about 1.5 mm; color as maturing between RHS 137A and RHS 146A and when mature nearest RHS 161B;

Seed: Typically about 50 per capsule; endospermic; flattened-elliptic wing surrounding embryo situated toward one end of ellipse; up to about 11.0 mm long and 3.0 mm wide and 1.0 mm thick at embryo; color nearest RHS 202A;

Disease tolerance and resistance: The new plant has not shown any resistance to pests and diseases common to *hostas*. The plant grows best and shows best coloration with plenty of moisture, adequate drainage and light sun, but is able to tolerate some drought when mature. Hardiness at least from USDA zone 3 through 9, and other disease resistance is typical of that of other *hostas*.

It is claimed:

1. A new and distinct ornamental plant cultivar named *Hosta* 'Age of Gold' as herein described and illustrated.

* * * * *